United States Patent [19]

Hennart et al.

[11] 3,962,415

[45] June 8, 1976

[54] INSECTICIDE EVAPORATOR COMPRISING DDVP WITH SYNERGIZED BENZODIOXOLE COMPOUND AS STABILIZER

[75] Inventors: Claude Hennart, Aubervilliers; Marcel Louis Dulat, Poitiers, both of France

[73] Assignee: Airwick Industries, Inc., Carlstadt, N.J.

[22] Filed: July 17, 1973

[21] Appl. No.: 380,129

Related U.S. Application Data

[63] Continuation-in-part of Ser. No. 180,507, Sept. 14, 1971, Pat. No. 3,852,439.

[52] U.S. Cl. ................................. 424/19; 424/33; 424/83; 424/175; 424/219; 424/282
[51] Int. Cl.² .................... A01N 17/00; A01N 9/36
[58] Field of Search .............. 424/175, 33, 219, 83, 424/282, 19

[56] References Cited
UNITED STATES PATENTS

| | | | |
|---|---|---|---|
| 3,155,568 | 11/1964 | Surgant et al. | 424/175 |
| 3,338,783 | 8/1967 | Popjak | 424/219 |
| 3,620,453 | 11/1971 | Gancberg et al. | 424/219 |
| 3,705,941 | 12/1972 | Hennart et al. | 424/219 |

OTHER PUBLICATIONS

Chemical Abstracts, vol. 74 (1971), p. 31083m.

*Primary Examiner*—V. D. Turner
*Attorney, Agent, or Firm*—Wenderoth, Lind & Ponack

[57] ABSTRACT

Insecticide evaporator comprising at least one volatile phosphoric ester insecticide, an agent for stabilising the said ester against decomposition by protonisation and used in an amount of 0.2 to 10 % based on the weight of phosphoric ester, characterised in that the stabilising agent contains at least one compound selected from the compounds of the chemical class of 1,3-benzodioxoles and the balance of said stabilising agent being selected from elemental sulphur, a compound of divalent sulphur, a diazene and an epoxidized compound.

9 Claims, No Drawings

3,962,415

INSECTICIDE EVAPORATOR COMPRISING DDVP WITH SYNERGIZED BENZODIOXOLE COMPOUND AS STABILIZER

RELATIONSHIP TO EARLIER APPLICATION

This application is a continuation-in-part of our pending patent application Ser. No. 180,507 filed on Sept. 14, 1971, now U.S. Pat. No. 3,852,439.

BACKGROUND OF THE INVENTION

Volatile phosphoric esters are now widely used as pesticides, particularly as evaporator insecticides. Their wide use is due principally to their rapid action as vapors and the absence of any accumulation of the compounds in living tissue as a result of their rapid hydrolysis in situ.

This last characteristic, which gives a net advantage over "chlorinated" pesticides, is on the other hand, a serious disadvantage: the sensitivity of certain phosphoric acid esters to humidity, even just that of the atmosphere, is such that decomposition takes place in the evaporator before evaporation and before they are able to act on the pest organisms. The esters particularly susceptible to this are those containing low alkyl groups such as methyl, ethyl, propyl or isopropyl attached to the phosphoric anion. On contact with molecules of water, at least partial decomposition of the esters takes place by protonisation, i.e. by replacement of a low alkyl group by hydrogen.

Among the sensitive phosphoric esters, special mention should be made of 0-2,2-dichlorovinyl-0,0-dimethyl phosphate, better known by the common name of DICHLORVOS or DDVP, the use of which in permanent insecticidal devices, so-called evaporators, has risen very greatly during recent years.

Various methods of stabilisation of the sensitive phosphoric esters in the evaporator have already been suggested to limit the decomposition of there phosphoric esters, but they are generally toxic such as phenols, amines or low nitrogen heterocyclics; another class of useful stabilizers includes azoic and hydrazonic compounds, but these possess a strong colouring ability which does not always permit them to be used. The use of anhydrides or epoxides has also been suggested, but it is known that these compounds act by fixation either of a molecule of water or of a molecule of free acid: it is clear that this process is stoichiome trically limited and that stabilisation ceases when all the stabiliser has reacted. This leads to the necessity of using substantial proportions of these stabilisers, which is not economic.

OBJECT AND SUMMARY OF THE INVENTION

It is an object of the present invention to stabilise volatile pesticidal phosphoric esters in an evaporator, by using substances more efficacious and not having the disadvantages stated above.

Certain benzodioxole derivatives have been suggested as insecticidal synergists, i.e. as reinforcing agents for the insecticidal action on contact with the insects, these being at very high concentrations of the order of 200 to 500% taken on the basis of the total weight of insecticidal compound. It has never been found, before the present invention, that the benzodioxole derivatives, particularly at low concentrations, are useful for preserving phosphoric esters present in evaporators against the protonisation occuring during stocking and use.

This invention accordingly provides an insecticide evaporator comprising: 1. an insecticidally effective amount of a volatile insecticidal phosphoric ester selected from a di($C_1$-$C_3$ alkyl)-dihalogenomethyl-vinyl-phosphate dihalogenomethyl-vinyl-phosphate and a tetrahalogeno ($C_2$ or $C_3$ alkyl) di ($C_1$ or $C_2$ alkyl) phosphate, wherein the halogen substituents are chlorine or bromine, II. from about 0.2 or 30%, based on the weight of the volatile phosphoric ester, of a stabilising agent consisting essentially of about 0.1 to 10%, based on the weight of the volatile phosphoric ester, of benzodioxole stabilizer and the balance of said stabilising agent is selected from elemental sulphur, a divalent sulphur compound, a diazene, and an epoxidized compound. This evaporator may optionally comprise a solvent for the phosphoric ester, which may be solid or liquid, under pressure or otherwise. It may also optionally comprise one or more inert mineral or organic adjuvants.

According to a preferred embodiment, the present invention also includes evaporators comprising ingredients (A) and (B) above, and furthermore including: (C) at leat one second agent stabilising the said pesticidal phosphoric ester against protonisation, this second agent being selected from elemental sulphur, compounds of divalent sulphur such as those defined in U.S. Pat. application Ser. No. 180,137 filed on even date herewith, from diazenes such as those defined in U.S. application Ser. No. 17,918 filed 11th Mar. 1970 and from epoxidized compounds.

This second stabilising agent augments the stabilising effect of the principal agent in a fashion showing a pronounced synergistic stabilisation action.

According to a preferred embodiment of the invention, the proportion of an epoxidized compound present ranges from about 0.1 to 20%, the proportion of a diazene ranges from about 0.1 to 10%, the proportion of a compound of divalent sulphur ranges from about 0.05 to 10% and the proportion of elemental sulphur from about 0.05 to 6%, all percentages being on the weight of the said volatile phosphoric ester.

When the insecticide evaporator is constituted by an impregnated support, the latter can be enveloped in a permeable membrane consisting of a layer of polyethylene or polypropylene or a mixture thereof, or of a copolymer of ethylene and propylene, or of a copolymer comprising vinylidene chloride.

According to a preferred embodiment of the invention, the said permeable membrane is constituted by a layer of polyethylene having a thickness of from about 10 to 80 microns.

In preferred evaporators according to the invention, the stabilising agent essentially consists of a mixture of a benzodioxole substituted by an unsaturated aliphatic group and elemental sulphur or of a mixture of a benzodioxole substituted by an unsaturated aliphatic group and a compound of divalent sulphur.

According to a preferred embodiment, the total proportion of stabilising agent is between 0.5 and 6% based on the weight of phosphoric ester. In the proportions suggested in the present invention, the benzodioxole has no action as toxicity synergist for the insecticidal phosphoric ester.

The preferred benzodioxoles for use in the present invention are defined by general formula I

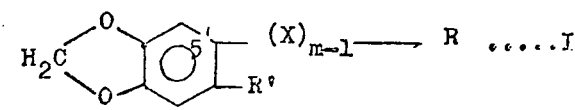 

wherein $m$ is 1 or 2, and X is an alkylene bridge of 1 to 7 carbon atoms, an alkenylen bridge of 2 to 7 carbon atoms or an alkadienylene bridge of 4 to 7 carbon atoms, and R' is one of the following
  a. hydrogen
  b. alkyl of 1 to 6 carbon atoms unsubstituted or substituted by phenyl or nitro.
  c. alkenyl of 2 to 6 carbon atoms, unsubstituted or substituted by phenyl or nitro,
  d. nitro
  e. halogen of atomic number not greater than 35
  f. low alkoxy, and A. $m$ representing only 1
R represents one of the following in formula I
  a. hydrogen
  b. low alkyl
  c. low alkenyl
  d. halogen of atomic number not exceeding 17
  e. nitro,
  f. the group

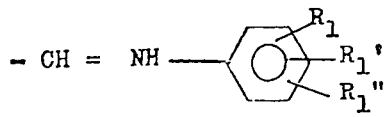

in which each of $R_1$, $R_1'$ and $R_1''$, independently of the others, is the same or a different group selected from the following: hydrogen, low alkyl, low alkoxy, hydroxy, nitro, chlorobromo and low alkylthio;
  g. the group

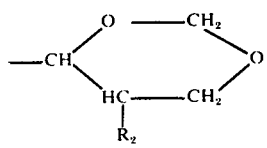

in which $R_2$ is hydrogen or low alkyl,
  h. the group

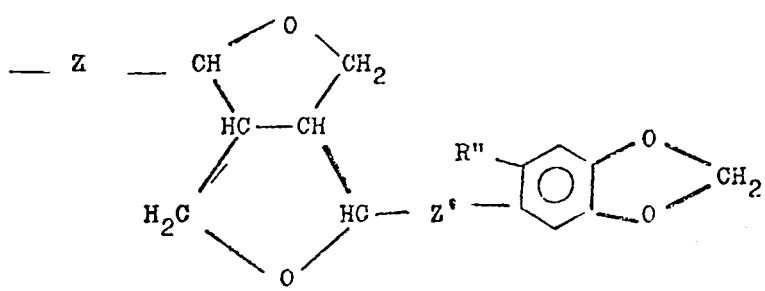

in which Z and Z' are each independently a C—C bond or an oxygen atom (—O—), and R'' is hydrogen, low alkyl or low alkoxy
  i. the group in which $R_3$ is alkyl of 1 to 6 carbon atoms or oxa-alkyl of at most 15 carbon atoms and having one or two atoms of oxygen in the chain B. $m$ representing 1 or 2
R represents one of the following constituents in formula I
  i. cyano
  ii. the group

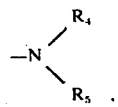

wherein $R_4$ is hydrogen, low alkyl or low alkanoyl, and $R_5$ is hydrogen or low alkyl,
or $R_4$ and $R_5$ together with the nitrogen atom to which they are attached, constitute a pyrrolidino, piperidino, morpholino or azepino group, unsubstituted or substituted by low alkyl,
  iii. the group —CO—$R_6$ in which $R_6$ is one of the following constituents:
    a. hydrogen
    b. —OM in which M is hydrogen or an equivalent metal ion
    c. low alkyl
    d. low alkoxy
    e. alkoxyalkoxy of 2 to 7 carbon atoms
    f. alkoxyalkoxyalkoxy of 4 to 10 carbon atoms
    g. phenyl, unsubstituted or substituted by one or more of the following substituents: low alkyl, low alkoxy, chloro, bromo;
    h. the group

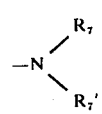

wherein each or $R_7$ and $R_7'$ is independently selected from hydrogen, low alkyl or phenyl
  iv. the group

in which the alkyl group has 1 to 8 carbon atoms
  v. the group —O—$R_8$ in which $R_8$ is low alkyl or oxa alkyl of at most 15 carbon atoms and 3 oxygen atoms in the chain.

vi. the group

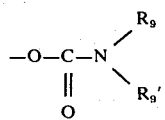

in which each of $R_9$ and $R_9'$ independently is hydrogen or low alkyl, or $R_9$ and $R_9'$ taken together with the nitrogen atom to which they are bond, constitute a pyrrolidino, piperidino, morpholino or azepino group, or c. $m$ representing 1

R and R' taken together represent one of the following divalent groups:

a. the group

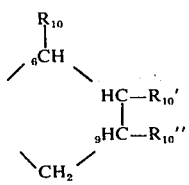

in which each of $R_{10}$, $R_{10}'$ and $R_{10}''$ independently is hydrogen, low alkyl, alkoxycarbonyl of 2 to 5 carbon atoms, or the group —COOM, M having the meaning given above, or B. the group

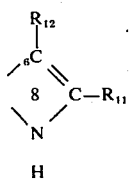

in which $R_{11}$ is one of the following constituents, hydrogen, low alkyl, low alkoxy, low alkanoyl or benzoyl, and $R_{12}$ represents one of the following constituents:

hydrogen, low alkyl, low alkoxy or the group

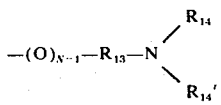

wherein $n$ is 1 or 2

$R_{13}$ is an alkylene bridge of 2 to 4 carbon atoms, and each of $R_{14}$ and $R_{14}'$ independently, is hydrogen or low alkyl, or $R_{14}$ and $R_{14}'$ taken together with the nitrogen atom to which they are bound, are a pyrrolidino, piperidino, mor pholino or azepino group.

The organic constituents noted above for formula I and qualified above and in what follows, and in the claims, by the term "low" have at most 6 carbon atoms and preferably 1 to 4 carbon atoms.

Included also within the benzodioxoles of formula I are the more or less volatile addition salts formed between benzodioxoles having a basic function and suitable organic or mineral acids. The term metallic ion, used in defining M above, includes ammonium ions $NR_wR_xR_yR_z$ in which $R_w$, $R_x$, $R_y$ and $R_z$ each independently represent hydrogen or an organic group, chiefly low alkyl.

The term benzodioxole used in the following examples and claim always means 1,3-benzodioxole.

Particularly preferred benzodioxoles among those defined by formula I above, are chosen from the following classes:

1. Simple benzodioxoles defined by formula I'

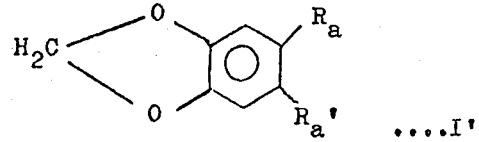

wherein $R_a$ is chosen from:
hydrogen, fluorine, bromine, alkyl of 1 to 6 carbon atoms, unsubstituted or substituted by nitro or phenyl, alkenyl of 2 to 4 carbon atoms, nitroalkenyl of 2 to 4 carbon atoms, styryl and nitro,
and $R_a'$ is chosen from:
hydrogen, fluorine, chlorine, bromine and alkyl of 1 to 6 carbon atoms.

Such compounds are, for example, the following:
a. 5-nitro benzodioxole
c. 5-fluoro benzodioxole
d. 5-chloro benzodioxole
e. 5-bromo benzodioxole
f. 5,6-dichloro benzodioxole
g. 5,6-dibromo benzodioxole
h. 5-methyl benzodioxole
i. 5-propyl benzodioxole
j. 5-isobutyl benzodioxole
k. 5-tertbutyl benzodioxole
l. 5-hexyl benzodioxole
m. 5-methyl 6-propyl benzodioxole
n. 5,6-dimethyl benzodioxole
o. 5—(2-nitro propyl) benzodioxole
p. 5vinyl benzodioxole
p. 5-allyl benzodioxole
r. 5-(propen-l-yl) benzodioxole
s. 5-methallyl benzodioxole
t. 5-allyl 6-methyl benzodioxole
u. 5-allyl 6-butyl benzodioxole
v. 5-styryl benzodioxole
w. 5—(2-nitro vinyl) benzodioxole
x. 5-(2-nitro propen-l-yl) benzodioxole
y. 5-benzyl benzodioxole;

2. Carbonylated benzodioxoles defined by formula II

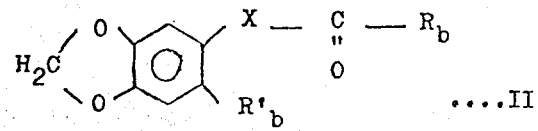

in which X is a direct bond or is an alklene or alkeylene group, each of which contains at most 7 carbon atoms in straight or branched chain; $R_6{}^b$ is hydrogen or alkyl of 1 to 4 carbon atoms or phenyl optionally substituted by one or two low alkyl groups, or a carbamoyl group optionally substituted by one or two low alkyl groups or phenyl, and $R_6{}^{b'}$ represents hydrogen, low alkyl, chlorine, bromine, fluorine or nitro. Such compounds are, for example, the following:
  a. 5-formyl benzodioxole
  b. 5-chloro 6-formyl benzodioxole
  c. 5-formyl 6-nitro benzodioxole
  d. 5-(2-formyl vinyl) benzodioxole
  e. 5-acetyl benzodioxole
  f. 5-acetyl 6-methyl benzodioxole
  g. 5-propionyl benzodioxole
  h. 5-benzoyl benzodioxole
  i. 5-butyryl benzodioxole
  j. 5-(2-carbamoly ethyl) benzodioxole
  k. 5-(2-N-methylcarbamoyl ethyl) benzodioxole
  l. 5-(3-N-methylcarbamoyl propyl) benzodioxole
  m. 5-(1-methylcarbamoyl 2-propyl) benzodioxole
  n. 5-(2-N-butylcarbamoyl ethyl) benzodioxole
  o. 5-(2-N,N-dimethylcarbamoyl ethyl) benzodioxole
  p. 5-(2-N-phenylcarbamoyl ethyl) benzodioxole
  q. 5-(2-N,N-diphenylcarbamoyl ethyl) benzodioxole
  r. 5-(2-oxo propyl) benzodioxole
  s. 5-(3-oxo butyl) benzodioxole
  t. 5-(2-oxo butyl) benzodioxole
  u. 5-(2-oxo pentyl) benzodioxole
  v. 5-[2-(4-methyl benzoyl) vinyl]benzodioxole
  w. 5-(2-oxo hexyl) benzodioxole
  x. 5-benzoylmethyl benzodioxole
  y. 5-(3-oxo butene-1 yl) benzodioxole
  z. 5-(4-methyl benzoyl)methyl benzodioxole
  a'. 5-(3-oxo-2-methyl butene-1 yl) benzodioxole
  b'. 5-(2,4-dimethyl benzoyl)methyl benzoxioxole
  c'. 5-(3-oxo 2-methyl pentene-1 yl) benzodioxole
  d'. 5-(4-ethyl benzoyl)methyl benzodioxole
  e'. 5-(3-oxo 2-pentyl butene-1 yl) benzodioxole
  f'. 5-(3-oxo 2-ethyl butene-1 yl) benzodioxole
  g'. 5-(2-benzoyl ethyl) benzodioxole
  h'. 5-(3-benzoyl propyl) benzodioxole
  i'. 5-(3-oxo 2-isopropyl butene-1 yl) benzodioxole
  j'. 5-(2-benzoyl vinyl) benzodioxole
  k'. 5-(3-acetyl 2,2-diethyl propyl) benzodioxole
  l'. 5-(2-formyl ethyl) benzodioxole
  m'. 5-[2-(2,4 dichloro benzoyl) ethyl] benzodioxole
  n'. 5 [2-(4-bromo benzoyl) ethyl] benzodioxole
  n'. 5-(7-acetyl heptyl) benzodioxole
3. Carboxylated benzodioxoles defined by formula III

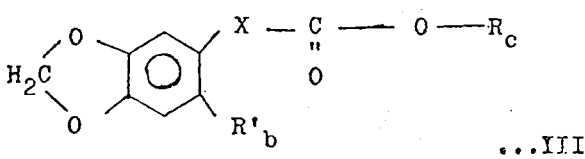

...III in which X and $R_b'$ are as defined in (2) above, and $R_c$ is hydrogen, alkyl of 1 to 4 carbon atoms or low alkenyl, or an oxa-alkyl group containing 3 to 7 carbon atoms or a dioxa-alkyl group containing 5 to 10 carbon atoms, or a phenyl group. Such compounds are, for example, the following:
  a. 5-carboxy benzodioxole
  b. 5-methyoxycarbonyl benzodioxole
  c. 5-ethoxycarbonyl benzodioxole
  d. 5-butoxy carbonyl benzodioxole
  e. 5-(2-ethoxy ethoxy)carbonyl benzodioxole
  f. 5-(3,6-dioxa decyl) oxycarbonyl benzodioxole
  g. 5-(2-carboxy vinyl) benzodioxole
  h. 5-(2-carboxy ethyl) benzodioxole
  i. 5-(2-carboxy hepten-1 yl) benzodioxole
  k. 5-(2-methoxycarbonyl vinyl) benzodioxole
  l. 5-(2-butoxy carbonyl vinyl) benzodioxole
  m. 5-(2-carboxy vinyl) 6-nitro benzodioxole
  n. 5-carboxy 6-nitro benzodioxole
  o. 5-ethoxycarbonyl 6-nitro benzodioxole
  p. 5-(carboxymethyl) benzodioxole
  q. 5-(4-carboxy butadien-1,3 yl) benzodioxole
  r. 5-carboxy 6-chloro benzodioxole
  s. 5-ethoxycarbonyl 6-methyl benzodioxole
  t. 5-phenoxycarbonyl benzodioxole
  u. 5-(phenoxycarbonyl-methyl) benzodioxole
  v. 5-allyloxycarbonyl benzodioxole.
4. Nitrilated benzodioxoles defined by formula IV

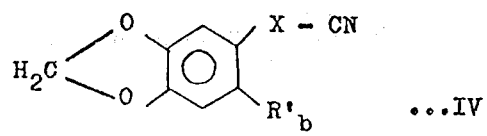

...IV in which X and $R_b'$ are as defined in 2) above. Such compounds are, for example
  a. 5-cyano benzodioxole
  b. 5-cyano 6-nitro benzodioxole
  c. 5-cyanomethyl benzodioxole
  d. 5-(2-cyano ethyl) benzodioxole
  e. 5-(2-cyano vinyl) benzodioxole
  f. 5-(2-cyano vinyl) 6-nitro benzodioxole
  g. 5-(2-cyano hepten-1 yl) benzodioxole
  h. 5-(5-cyano pentyl) benzodioxole
  i. 5-(2-cyano heptyl) benzodioxole
  j. 5-cyano 6-chloro benzodioxole
  k. 5-cyanomethyl 6-methyl benzodioxole.
5. Hydroxylated benzodioxoles of formula V.

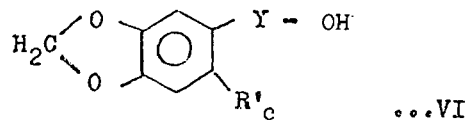

...VI in which Y is a direct bond or is alkylene of 1 to 4 carbon atom in straight or branched chain, or is low alkenylene, and $R_c'$ is hydrogen, methyl, bromine or chlorine. Such compounds are, for example:
  a. 5-hydroxy benzodioxole
  b. 5-hydroxymethyl benzodioxole,
  c. 5-(hydroxy-2 ethyl) benzodioxole
  d. 5-(hydroxy ethyl) benzodioxole
  e. 5-(3-hydroxy propyl) benzodioxole
  f. 5-(1-hydroxy propyl) benzodioxole
  g. 5-(1-hydroxy butyl) benzodioxole
  h. 6-chloro 5-hydroxymethyl benzodioxole
  i. 5-hydroxy 6-methyl benzodioxole
  j. 5-hydroxymethyl 6-methyl benzodioxole;
  k. 5-hydroxy 6-bromo benzodioxole
  l. 5-(3-hydroxy butene-1 yl) benzodioxole.
6. Aminated benzodioxoles defined by formula VI.

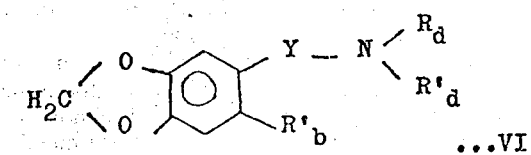

...VI wherein $R_b'$ and Y are as defined in (2) and (5) above respectively, and $R_d$ and $R_d'$ are the same or different and are each hydrogen or alkyl of 1 to 4 carbon atoms, or one of them can be alkanoyl of 1 to 4 carbon atoms, and also $R_d$ and $R_d'$ can represent, together with the nitrogen atom to which they are attached, pyrrolidino, piperidino, morpholino or azepino. Such compounds are, for example, the following:

a. 5-(N,N-dimethylamino) benzodioxole
b. 5-(N,N-dimethylaminomethyl) benzodioxole
c. 5-(2-amino propyl) benzodioxole
d. 5-(N-formyl N-methyl aminomethyl) benzodioxole
e. 5-(N-acetylaminomethyl) benzodioxole
f. 5-(2-N-butyrylamino propyl) benzodioxole
g. 5-(2-N-methylamino ethyl) benzodioxole
h. 5-(2-N,N-diethylamino butyl) benzodioxole
i. 5-(2-N,N-dibutylamino ethyl) benzodioxole
j. 5-piperidinomethyl benzodioxole
k. 5-(1-azepinyl methyl) benzodioxole
l. 5-(2-morpholino ethyl) benzodioxole
m. 5-(4-methyl piperidino) methyl benzodioxole
n. 5-(2-pyrrolidino ethyl) benzodioxole
o. 5-aminomethyl 6-nitro benzodioxole
p. 5-(2-amino propyl) 6-nitro benzodioxole
q. 5-(N,N-dimethylaminomethyl) 6-nitro benzodioxole
r. 5-piperidino benzodioxole
s. 5-(3-N,N-dimethylamino butene-1 yl) benzodioxole
t. 5-(2-N-methylamino ethyl) 6-isopropyl benzodioxole
u. 5-(2-amino propyl) 6-methyl benzodioxole
v. 5-(2-amino propyl) 6-chloro benzodioxole.

7. Benzoxazoles having a sulphoxide function defined by formula VII.

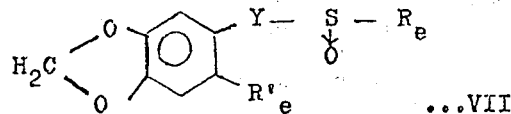

...VII wherein Y is as defined in 5) above, but is preferably an alkylene bridge $R_e$ is alkyl of 1 to 8 carbon atoms and $R_e'$ is hydrogen or alkyl of 1 to 4 carbon atoms. Such compounds are, for example, the following:

a. 5-(2-methylsulfinyl butyl) benzodioxole
b. 5-(2-butylsulfinyl ethyl) benzodioxole
c. 5-(2-butylsulfinyl propyl) benzodioxole
d. 5-(2-octyl sulfinyl propyl) benzodioxole
e. 5-(2-octylsulfinyl ethyl) benzodioxole
f. 5-(3-octylsulfinyl propyl) benzodioxole
g. 6-methyl 5-(2-octylsulfinyl propyl) benzodioxole
h. 6-propyl 5-(2-octylsulfinyl propyl) benzodioxole
i. 6-butyl 5-(2-octylsulfinyl propyl) benzodioxole
j. 5-(2-octylsulfinyl ethyl 6-chloro)benzodioxole;

8. Benzodioxoles having at least one ether group defined by formula VIII

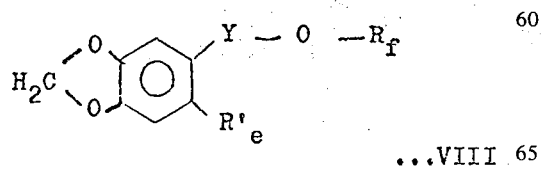

...VIII in which Y and $R_e'$ are as defined in (5) and (7) above respectively, and $R_f$ is alkyl of 1 to 4 carbon atoms or alkoxyalkyl of 2 to 7 carbon atoms, or alkoxyalkoxyalkyl of 4 to 10 carbon atoms, or alkoxyalkoxy alkoxy alkyl of 5 to 15 carbon atoms, or phenyl. Such compositions are, for example, the following:

a. 5-methoxy benzodioxole
b. 5-butoxy benzodioxole
c. 5-(2-ethoxy ethoxy) benzodioxole
d. 5-(2-ethoxy methyl) benzodioxole
e. 5-(2-methoxy propyl) benzodioxole
f. 5-(2-butoxy butyl) benzodioxole
g. 5-(2,5,8-trioxa dodecyl) benzodioxole
h. 5-methyl 6-(2,5,8-trioxa dodecyl) benzodioxole
i. 5-propyl 6-(2,5,8-trioxa dodecyl) benzodioxole
j. 5-butyl 6-(2,5,8-trioxa dodecyl) benzodioxole
k. 6-chloro 5-ethoxymethyl benzodioxole
l. 5-(3-methoxy butene-1 yl) benzodioxole
m. 5-phenoxymethyl benzodioxole
n. 5-ethoxy 6-nitro benzodioxole;
o. 5-(3,6,9-trioxa undecyl-2) oxy benzodioxole
p. 6-ethyl 5-(3,6,9-trioxa undecyl-2) oxy benzodioxole 9. Benzodioxoles having an acetal function defined by formula IX

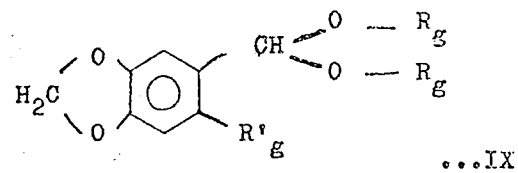

...IX in which $R_g$ is an alkyl group of 1 to 4 carbon atoms, or alkoxy alkyl of 2 to 7 carbon atoms or alkoxyalkoxy alkyl of 4 to 10 carbon atoms, and
$R_g'$ is hydrogen, chlorine, bromine, fluorine, nitro or low alkyl. Such compounds are, for example:

a. 5-(dimethoxy)methyl benzodioxole
b. 5-(diisobutoxy)methyl benzodioxole
c. 5-bis(2-ethoxy ethoxy) methyl benzodioxole
d. 5-bis (2-butoxy ethoxy)methyl benzodioxole
e. 5-bis(2-butoxy propoxy)methyl benzodioxole
f. 5-bis(3,6-dioxa decyloxy)methyl benzodioxole
g. 5-bis(5-methyl 4,7-dioxa dodecyloxy)methyl benzodioxole
h. 5-(dipropyloxy)methyl benzodioxole
i. 5-(dipropyloxy)methyl 6-chloro benzodioxole
j. 5-(dipropyloxy)methyl 6-nitro benzodioxole
k. 5-(dipropyloxy)methyl 6-methyl benzodioxole;

10. Benzodioxoles having a carbonic function defined by formula X

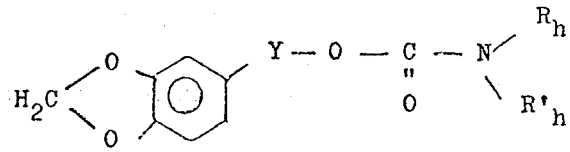

...X in which Y is as defined in (5) above, and $R_h$ and $R_h'$ are the same or different and are each hydrogen or alkyl of 1 to 4 carbon atoms, or are, together with the nitrogen atoms, piperidino, morpholino or pyrrolidino. Such compounds are, for example, as follows:

a. 5-carbamoyl oxy benzodioxole
b. 5-(N-methylcarbamoyl oxy) benzodioxole
c. 5-(N-butylcarbamoyl oxy) benzodioxole
d. 5-(N,N-dipropylcarbamoyl oxy) benzodioxole
e. 5-(N,N-pentamethylene carbamoyl oxy) benzodioxole
f. 5-carbamoyl oxy methyl benzodioxole
g. 5-(N,N-dimethylcarbamoyl oxy ethyl) benzodioxole
h. 5-(2-N,N-diethylcarbamoyl oxy ethyl) benzodioxole
i. 5-(2-N-butylcarbamoyl oxy butyl) benzodioxole
j. 5-(2-N,N-tetramethylene carbamoyl oxy propyl) benzodioxole
k. 5-(3-N-methylcarbamoyloxy butene-1 yl) benzodioxole
l. 5-morpholinocarbamoyloxymethyl benzodioxole
m. 5-N-isopropylcarbamoyloxy 6-methyl benzodioxole
n. 5-N-propylcarbamoyloxy 6-nitro benzodioxole
o. 5-N-ethylcarbamoyloxy 6-chloro benzodioxole
p. 5-piperidinocarbonyloxy benzodioxole;

11. Benzodioxoles carrying a dioxane ring defined by formula XI

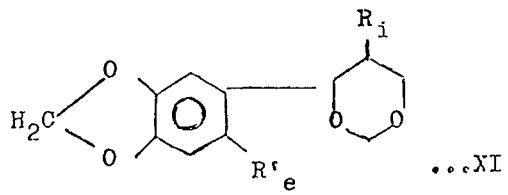

...XI in which $R_e'$ is as defined in (7) above and $R_i$ is hydrogen, methyl or ethyl. Such compounds are, for example:

a. 5-(4-dioxane -1,3 yl-4) benzodioxole
b. 5-(4-dioxane -1,3 yl-4) 6-methyl benzodioxole
c. 5-(4-dioxane -1,3 yl-4) 6-propyl benzodioxole
d. 5-[(4-(5-methyl dioxane-1,3)yl]benzodioxole
e. 5-[(4-(5-methyl dioxane-1,3)yl] 6-propyl benzodioxole
f. 5-[(4-(5-ethyl dioxane-1,3)yl] benzodioxole 12. Benzodioxole derivatives of tetraline defined by formula XII

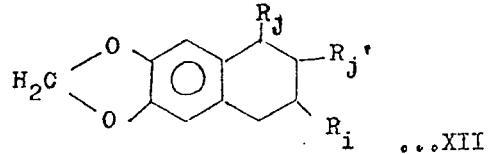

...XII in which $R_i$ is as defined in 11) above, and $R_j$ and $R_j'$ are the same or different and are each hydrogen, methyl, carboxy or alkoxycarbonyl containing in toto 2 to 5 carbon atoms. Such compounds are for example:

a. 5,6,7,8-tetrahydro naphtho-(2,3-d) 1,3-dioxole
b. 5,6,7-trimethyl5,6,7,8,-tetrahydro naphtho (2,3-d) 1,3-dioxole
c. 6,7-dimethyl 5,6,7,8-tetrahydro naphtho (2,3-d) 1,3-dioxole
d. 5,6-dicarboxy 5,6,7,8-tetrahydro naphtho (2,3-d) 1,3-dioxole
e. 5,6-dicarboxy 7-methyl 5,6,7,8-tetrahydro naphtho(2,3-d) 1,3-dioxole
f. 5,6-bis(ethoxy-carbonyl) 7-methyl 5,6,7,8-tetrahydro naphtho (2,3-d) 1,3-dioxole
g. 5,6-bis(propoxycarbonyl) 7-methyl 5,6,7,8-tetrahydro naphtho (2,3-d) 1,3-dioxole
h. 5,6-bis(butoxycarbonyl) 7-ethyl 5,6,7,8-tetrahydronaphtho(2,3-d) 1,3-dioxole 13. Benzodioxole derivatives of dioxabicyclooctane defined by formula XIII

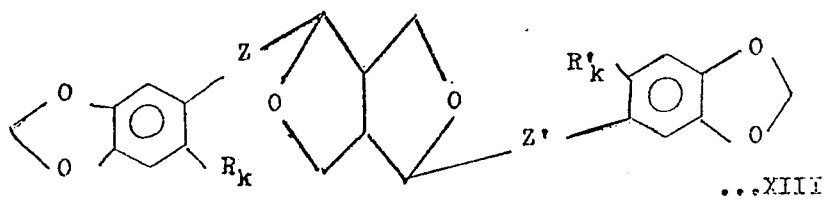

...XIII in which Z and Z' are the same or different and are each a direct bond or an oxygen atom; $R_k$ and $R_k'$ are the same or different and are hydrogen, methyl or methoxy. Such compounds are, for example:

a. 2,6-bis(5-benzodioxole-1,3 yl 3,7-dioxa bicyclo (3,30) octane
b. 2,6-bis(5-benzodioxole-1,3 yl oxy) 3,7-dioxa bicyclo (3,3,0) octane
c. 2-(5-benzodioxole-1,3 yl) 6-(5-benzodioxole-1,3 yl oxy) 3,7-dioxabicylo(3,3,0) octane
d. 2-(5-benzodioxole-1,3 yl) 6-(5-(6-methoxy benzodioxole-1,3 3 yl)) 3,7-dioxa bicyclo(3,3,0)octane
e. 2-(5-benzodioxole-1,3 yl)6-(5-(6-methyl-6 benzodioxole-1,3 yl)) 3,7-dioxa bicyclo(3,3,0)octane
f. 2,6-bis (5-(6-methoxy benzodioxole-1,3 yl)) 3,7-dioxa bicyclo (3,3,0)octane
g. 2,6-bis (5-(6-methyl benzodioxole-1,3 yl)) 3,7-dioxa bicyclo (3,3,0)octane 14. Benzodioxole derivatives of indole defined by formula XIV

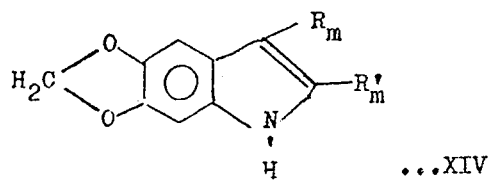

...XIV in which $R_m$ is hydrogen, alkyl of 1 to 4 carbon atoms or alkoxy of 1 to 4 carbon atoms, each of these groups optionally bearing a group

as defined in (10) above, $R_m'$ is hydrogen, alkyl of 1 to 4 carbon atoms, alkoxy of 1 to 4 carbon atoms, alkanoyl of 2 to 4 carbon atoms or benzoyl. Such compounds are, for example, the following a. (1,3 dioxolo) [4,5-f]indole
b. 3-methyl (1,3 dioxolo) [4,5-f] indole
c. 3-ethyl (1,3 dioxolo) [4,5-f] indole
d. 3-butyl (1,3 dioxolo) [4,5-f] indole
e. 2,3-dimethyl (1,3 dioxolo) [4,5-f]indole
f. 3-methoxy (1,3 dioxolo) [4,5-f] indole
g. 3-isobutoxy (1,3 dioxolo) [4,5-f] indole
h. 2,3-dimethoxy (1,3 dioxolo) [4,5-f]indole
i. 2-ethyl 3-methoxy (1,3 dioxolo) [4,5-f]indole
j. 3-(2-N,N-dimethylamino ethyl) (1,3 dioxolo) [4,5-f] indole
k. 3-(3-N-ethylamino propyl) (1,3 dioxolo) [4,5-f] indole
l. 3-(2-amino ethoxy) (1,3 dioxolo) [4,5 -f]indole
m. 3-(2-N,N-diethylamino ethoxy) (1,3 dioxolo) [4,5-f] indole
n. 3-(2-pyrrolidino ethoxy) (1,3 dioxolo) [4,5-f] indole
o. 3-(2-piperidino ethoxy) (1,3 dioxolo) [4,5-f] indole
p. 2-acetyl 3-(2-pyrrolidino ethoxy) (1,3 dioxolo) [4,5-f] indole
q. 2-butyryl 3-(2-pyrrolidino ethoxy) (1,3 dioxolo) [4,5-f] indole
r. 3-benzoyl 3-(2-pyrrolidino ethoxy) (1,3 dioxolo) [4,5-f] indole;

15. Benzodioxoles carrying an imine function defined by formula

XV

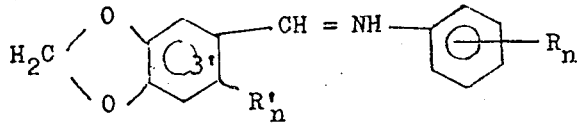

in which $R_n$ represents one to three substituents optionally chosen from alkyl of 1 to 4 carbon atoms, alkoxy of 1 to 4 carbon atoms, chloro, bromo, nitro, hydroxy and methyl thio. Such compounds are, for example, the following anilines N-substituted by piperonylidene a. aniline
b. 4-methyl aniline
c. 4-butyl aniline
d. 2,4-dimethyl aniline
e. 4-methoxy aniline
f. 2,4-dimethoxy aniline
g. 2,4,6-trimethoxy aniline
h. 4-butoxy aniline
i. 3-nitro aniline
j. 5-chloro 2,4-dimethoxy aniline
k. 2-chloro aniline
l. 2,3-dichloro aniline
m. 4-chloro 2-methyl aniline
n. 4-methylthio aniline
o. 2-bromo 4-nitro aniline
p. 2-hydroxy aniline
q. 5-chloro 2-methyl aniline
r. 4-bromo aniline
s. 2,5-dichloro aniline
t. 2,3,5-trichloro aniline
u. 2,4,6-trimethyl aniline
v. 4-t-butyl aniline and the following anilines x. N-(3'-chloro piperonylidene)-aniline
y. N-(3'-methyl piperonylidene)-(4-methyl aniline)
z. N-(3'-nitro piperonylidene)-(3-nitro aniline);

16. Salt derivatives of benzodioxoles, having an acid or phenolic function defined in (3), (5) and (12) above, these salts containing as cation a metal such as sodium, potassium, calcium, zinc, cadium, copper, nickel, cobalt, iron, manganese, silver, lead, barium, strontium and aluminium, or an ammonium ion derived from ammonia, an amine derivative containing 1 to 3 alkyl groups and 1 to 4 carbon atoms, for example methylamine, dimethylamine, trimethylamine, diethylamine, triethylamine, butylamine, dibutylamine and tributyl amine, or a heterocyclic nitrogen derivative, e.g. pyridine, morpholine, N-methyl morpholine, piperidine and pipercolines.

Such salts are, for example the following:

the sodium salts of compounds III (a), III (g), III (n), III (r), V (a), XII (d) and XII (e);

the ammonium salts of compounds III (a), III (h), III (m), III (p), V (i) and XII (d);

the neutral zinc salts of compounds III (a), V (a) and XII (e).

The use of these salts is of particular value when the phosphoric ester used has already undergone some protonisation; the salt introduced as stabiliser then acts as a first stage as a neutraliser for the acid phosphoric ester by exchanging its cation therewith for a proton; this neutralisation fovours the stabilisation since it has been observed by the applicants that the preservation of phosphoric esters is better when they do not contain any acid by-products; the benzodioxole, having lost its cation, keeps its stabilising properties and then acts for a second time.

17. Salt derivatives of benzodioxoles having a basic funtion defined in (6) and (14) above, these salts being formed with a mineral acid such as hydrochloric, sulphuric, carbonic, boric, hydrobromic or phosphoric acid, or an organic mono- or dicarboxylated acid such as acetic, propionic, benzoic, succinic, adipic, phthalic, maleic or phenylacetic acid. Such salts are, for example, the following:

a. to o.: the chlorid, sulphate, carbonate, borate, bromide, hydrogenphosphate, dihydrogen phosphate, acetate, propionate, benzoate, succinate, adipate, phthalate, maleate and phenylacetate of 5-(N,N-dimethylamino)benzodioxole (VI(a))

p. to z. and a'. to d'.: the salts of the same acids as in (a) to (o) just noted of (1,3-dioxolo [4,5-f] indole (XIV(a)).

The solvents for the phosphoric ester may advantageously be aliphatic alicylic or aromatic hydrocarbons, which are solid or liquid at ambient temperature with or without pressure. Such solvents may be used separately or in admixture. Their solvent action for the phosphoric ester and/or the benzodioxols can be optionally reinforced by the addition of co-solvents which may be selected from aliphatic ketones, hydroxylated compounds, ethers, esters, amides, nitriles and halogenated hydrocarbons containing at most 12 carbon atoms. Other solvents usable in evaporators according to the present invention are halogenated hydrocarbons containing at most 12 carbon atoms, ethers and esters formed between aliphatic, cycloaliphatic or aralkoylic alcohols or phenols, and aliphatic acids or di-acids such as phthalic acid, sebacic acid or adipic acid, or even non-pesticidal phosphoric esters such as the phosphoric triesters of methyl, ethyl, butyl, octyl, decyl, dodecyl, phenyl, cresyl, diphenyl, tert. butylphenyl etc. Solvents used in the evaporators according to the present invention may also be solid compounds, for example synthetic organic resins such as homopolymers and copolymers of vinyl derivatives (acetate, propionates, butyrate, oxides, formal, acetal, butyral, chloride etc.) and/or vinylidene or alkene derivatives (ethylene, propylene, butylene etc.) and/or styrene, and/or vinyl pyrrolidone, and/or cellulose derivatives (methyl oxide, ethyl oxide, benzyl oxide, acetate, propionate, butyrate phthalates, nitrate, etc.) and/or isoprene and/or butadiene and/or acrylic or methacrylic esters and/or allyl esters (phthalate, isophthalate, maleate, cyanurate, etc) and also synthetic resins of the type arising from the interaction of compounds with reactive groups, as is the case with the so called "epoxy" resins, formed by the condensation of an epoxide with a polyphenol, polyester resins formed by the action of a poly-acid with a polyol, polyurethane resins formed by condensation of a polyisocyanate with a polyol, or coumarone-indene type resins.

Solid compounds serving as solvents may also be natural resins, for example colophony, shellac, tallol or a waxy resin.

Amongst mineral adjuvants which may be introduced into evaporators according to the present invention, the following should be noted: brick, pumice, vermiculite, kaolin, dried clay, calcium carbonate, pyrophllite, dolomite, glass fibre, plaster, talc, natural silica, fossil or otherwise, synthetic silica and metallic oxides. Among inert organic adjuvants which may be introduced into the evaporators according to the present invention there should be noted: wood flour, cellulose fibre, starch, maize, faecula, sugars and/or diluents with little solvent action such as paraffin, there being optionally modified in their properties by the addition of synthetic organic resins and/or salts formed by alkoylamino-alkoylamines and aliphatic acids, and/or amine derivatives of montmorillonite such as bentones.

The complementary stabilisers are advantageously selected from sulphur, compounds of divalent sulphur, oxiranes, azoic compounds, their metalliferous derivatives and epoxidized compounds. Evaporators according to the present invention can also contain one or more natural or synthetic aromatic materials, complementary active agents such as an acaricide, an insectifugal agent, a bird-repellent, an antigungal agent or a bactericide.

The evaporator of the invention can be constituted by a solid or a liquid disposed on a solid porous or fibrous support. This support may be formed, for example, by a paper, a felt of wool, cotton and/or synthetic fibre, compressed cellulose such as wood fibre, cereals, alfalfa or cotton, a felt card, a card of old papers or a card of glass fibre.

EXPERIMENTS AND EXAMPLES ILLUSTRATING THE INVENTION

The presence of the benzodioxole as stabiliser confers stability to the phosphoric acid ester by water contained in the evaporator used in the ambient humidity, as is shown by the following exemplary experiments.

EXPERIMENT A 10 cm by 10 cm squares cut from a cellulose card made by the French company FIORONI S. A. under their reference 200 were used. At the time of use, the card weighed 870 g/m$^2$, i.e. 8.7 gm per square. The card squares were divided into three groups of three units numbered A-O to A-2. Cards A-O were impregnated with 12.5 g DDVP and the other cards were impregnated with 12.5 g of a solution in DDVP of one of the following compounds at a concentration of 1%.

A-1: 5(2-octylsulphinylpropyl) benzodioxole.

A-2: 5-propyl-6-(2,5,8-trioxadodecyl) benzodioxole.

The thus impregnated squares were suspended in a room of which the temperature was maintained at 22° ± 2° C, and the relative humidity of which was about 40.

At the end of 15 days the quantity of DDVP destroyed by hydrolysis was measured potentio metrically (it having been established elsewhere that hydrolysis of DDVP in the conditions given above leads to an acid phosphoric ester and that the potentiometric measurement of the single acidity or of the first acidity of this ester allows the quantity of DDVP hydrolysed to be measured).

Account was taken of the acidity present in the DDVP and this was deducted from the results obtained.

The percentage quantities of DDVP decomposed by hydrolysis which were formed are compiled in the table below. In the table, the values qualified by I represent the spread of results in each test:

| A-0 | A-1 | A-2 |
|---|---|---|
| 29.9 | 0.2 | 0.4 |
| ±1.9 | ±0.03 | ±0.1 |

EXPERIMENT B

Squares of card were used as in experiment A, but of size 5 x 10 cm and bonded in pairs, back to back, by staples, at the time of use, the card weighted 895 g/m$^2$; these double cards were divided into four groups numbered B-O to B-3. Each square B-O was impregnated with 12.5 g of DDVP and the other doubled cards were each impregnated with 12.5 g of a 1.5% solution, in DDVP, of one of the following compounds:

B-1 5-allyl benzodioxole
B-2 5-formyl benzodioxole

The thus impregnated cards were suspended in a room of which the temperature was kept at 22° ± 2° C and of which the relative humidity was about 70.

At the end of 15 days, the quantity of DDVP destroyed by hydrolysis was measured as in Experiment A, the percentage quantities of DDVP destroyed so determined are indicated in the following table.

| B-0 | B-1 | B-2 |
|---|---|---|
| 33.8 | 0 | 0.7 |
| ±2.9 | — | ±0.2 |

EXPERIMENT C

Doubled cards were used as in experiment B but in which the card weight was 885 g/m$^2$. These doubled cards were divided into four series C-O to C-3. The double cards C-O were each impregnated with 12.5 g of DDVP, the other doubled cards being each impregnated with 12.5 g of a 2% solution in DDVP of one of the following compounds:

C-1: 5-(3,6,9-trioxa undecyl-2-oxy) benzodioxole
C-2: 5,6-bis(propyoxycarbonyl)-7-methyl-5,6,7,8-tetrahydro naphtho (2,3,-d)-1,3-dioxole
C-3: an equimolecular mixture of 2,6-bis(5-benzodioxole-1, 3-yl)-3,7-dioxabicyclo(3,3,0) octane and 2-(5-benzodioxole-1,3-yl)-6-(5-benzodioxole-1,3-yl-oxy)-3,7-dioxabicyclo(3,3,0) octane The thus impregnated cards were suspended in a room the temperature of which was kept at 22° ± 2° C and of which the relative humidity was about 65.

At the end of 15 days, the percentage quantity of DDVP destroyed was measured as in Experiment I and is tabulated as follows:

| C-0 | C-1 | C-2 | C-3 |
|---|---|---|---|
| 45.8 | 0.02 | 2.9 | 1.9 |
| ±2.5 | ±0.002 | ±0.4 | ±0.2 |

EXPERIMENT D

Doubled cards were used as in Experiment B, but of weight 890 g/m$^2$. These doubled cards were divided into nine series numbered D-O to D-8; the cards D-O were each impregnated with 12.5 g of a 3% solution in DDVP of one of the following compounds:

D-1: 5-hydroxy benzodioxole
D-2: 5-hydroxymethyl benzodioxole
D-3: 5-(propen-1 yl) benzodioxole
D-4: 5-acetonyl benzodioxole
D-5: 5-(3-oxo-buten-1 yl) benzodioxole
D-6: 5-cyanomethyl benzodioxole
D-7: 5-(2-amino propyl) benzodioxole
D-8: 5-(5-methyl 4-dioxane -1,3 yl) benzodioxole The thus impregnated cards were suspended in a room of the temperature of which was kept at 22° ± 2° C and the relative humidity of which was between 70 and 75.

At the end of 12 days, the percentage quantities of DDVP destroyed were measured as in Experiment A and tabulated as follows:

| D-0 | D-1 | D-2 | D-3 | D-4 | D-5 | D-6 | D-7 | D-8 |
|---|---|---|---|---|---|---|---|---|
| 41.3 | 0 | 0.3 | 0 | 9.2 | 0.8 | 3.4 | 0 | 2.1 |
| ±1.1 | — | ±0.02 | — | ±1.0 | ±0.07 | ±0.2 | — | ±0.2 |

EXPERIMENT E

Doubled cards as described in Experiment B were used, but of weight 910 g/m$^2$. These cards were divided into six series numbered E-O to E-5. The double cards E-O were each impregnated with 12.5 g of DDVP; the other doubled cards were each impregnated with 12.5 g of a solution in DDVP of the following compounds in the concentrations given:

E-1 2% of 5-benzoylmethyl benzodioxole
E-2 2% of benzodioxole
E-3 2% of 5-bromo benzodioxole
E-4 2% of 5-nitrobenzodioxole
E-5 5% of 5-cyanobenzodioxole.

The thus impregnated cards were suspended in a room the temperature of which was kept at 22°± 2° C and the relative humidity of which was about 74.

At the end of 15 days the percentage quantities of DDVP destroyed were measured as in Experiment A and tabulated as follows:

| E-0 | E-1 | E-2 | E-3 | E-4 | E-5 |
|---|---|---|---|---|---|
| 49.5 | 0 | 4.1 | 4.3 | 0.6 | 1.7 |
| ±0.8 | — | ±0.6 | ±0.5 | ±0.03 | ±0.5 |

EXPERIMENT F

Doubled cards were used as in Experiment B but of weight 835 g/m$^2$. These cards were divided into 8 series numbered F-O to F-7. Each card of F-O was impregnated with 12.5 g DDVP while the other cards were each impregnated with a 3% solution in DDVP of one of the following compounds:

F-1 5(2-N-phenylcarbamyl ethyl) benzodioxole
F-2 5[2-(4-methylbenzoyl)vinyl]benzodioxole
F-3 5-propyl benzodioxole
F-4 5(2-nitrovinyl) benzodioxole
F-5 N-piperonylidene (4-methyl aniline)
F-6 N-piperonylidene (5-chloro-2,4 dimethoxy aniline)
F-7 5-methoxy benzodioxole.

The thus impregnated cards were suspended in a room the temperature of which was kept at 21° ± 1° C and the relative humidity of which was about 65.

At the end of 15 days, the percentage quantities of DDVP destroyed were measured as noted in Experiment A and tabulated as follows:

| F-0 | F-1 | F-2 | F-3 | F-4 | F-5 |
|---|---|---|---|---|---|
| 34.2 | 0 | 0.2 | 0 | 1.3 | 3.4 |
| ±0.8 | — | ±0.02 | — | ±0.1 | ±0.3 |
| F-6 | F-7 | | | | |
| 7.1 | 0 | | | | |
| ±0.4 | — | | | | |

EXPERIMENT G

Doubled cards were used as described in Experiment B above but in which the weight was 910 g/m$^2$. These cards were divided into six series called G-0 to G-5. The double cards G-0 were each impregnated with 12.5 g of DDVP.

The other double cards were each impregnated with 12.5 g of 4% solution in DDVP of one of the following compounds:

G-1: sodium 7-methyl-5,6,7,8-tetrahydronaphtho [2,3-d]1,3 dioxole 5,6-dicarboxylate
G-2 zinc 3(5-benzodioxole) acrylate
G-3: piperidine 3-(5-benzodioxole) acrylate
G-4: lead 3-(5-benzodioxole) acrylate
G-5: piperidine 5-benzodioxole carboxylate The thus impregnated cards were suspended in a room the temperature of which was kept at 22° ± 2°C and of which the relative humidity was about 75.

At the end of 10 days, the percentage quantities of DDVP destroyed were measured as given in Experiment A and tabulated as follows:

| G-0 | G-1 | G-2 | G-3 | G-4 | G-5 |
|---|---|---|---|---|---|
| 36.8 | 1.9 | 2.8 | 5.6 | 5.0 | 5.4 |

EXPERIMENT H

Doubled cards were used as in Experiment B but of weight 910 g/m². The cards were divided into three series denoted H-0, H-1, and H-2. The doubled cards H-0 were each impregnated with 12.5 g of DDVP.

The other double cards were each impregnated with 12.5 g of a solution in DDVP of the hydrochloride of 2-benzoyl 3-(2-pyrrolidinoethoxy) (1,3-dioxolo)[4,5-f] indole at the following concentrations:
H-1 0.2%
H-2 0.5%

The thus impregnated cards were suspended in a room the temperature of which was kept at 22° ± 2°C, and of which the relative humidity was about 80.

At the end of 15 days, the percentage quantities of DDVP destroyed were measured as noted in Experiment A and the results tabulated as follows:

| H-0 | H-1 | H-2 |
|---|---|---|
| 57.5 | 1.4 | 1.1 |
| ± 6.8 | ±0.1 | ±0.1 |

The result of Experiments A, B, C, D, E, F, G and H show clearly that what extent DDVP is susceptible to humidity when unprotected: they also shown that the hydrolysis can be reduced by a substantial amount when a benzodioxole is added to this phosphoric ester.

EXPERIMENT I

Doubled cards were used as described in Experiment B but of weight 905 g/m². These doubled cards were divided into six series I - 0 to I - 5. Each card I - 0 was impregnated with 12.5 g of DDVP. The other double cards were each impregnated with 12.5 g of a solution in DDVP as follows:
I-1: 1.7% of 1-(4-methyl-2-nitrophenyl azo)-3-ethoxycarbonyl-4,4-dimethyl-1,2,6-dioxo cyclohexane.
I-2: 1.7% of 5-allyl benzodioxole
I-3: 1% of 5-allyl benzodioxole + 0.7% of 1-(4-methyl-2-nitro phenylazo)-3-ethoxycarbonyl-4,4-dimethyl-2,6-dioxo cyclohexane.
I-4: 1.7% of 5-(3-oxo-butene-1 yl) benzodioxole
I-5: 1% of 5-3-oxo butene-1 yl) benzodioxole + 0.7% of 1-nitro-4 methyl-2 phenlazo-3-ethoxycarbonyl-4,4-dimethyl-2,6-dioxo-cyclohexane.

The thus impregnated cards were suspended in a room the temperature of which was kept at 22°±2°C, and of which the relative humidity was about 77.

At the end of 21 days, the quantities of DDVP destroyed were measured as given in Experiment A and tabulated as follows:

| I-0 | I-1 | I-2 | I-3 | I-4 | I-5 |
|---|---|---|---|---|---|
| 45.1 | 16.2 | 1.2 | 0.7 | 7.1 | 0.9 |
| ±0.7 | ±1.9 | ±0.3 | ±0.1 | ±1.3 | ±0.1 |

The results of this experiment show the value of mixtures of stabilizers according to the invention with stabilisers of the family of azoic compounds. It can in effect be seen from the foregoing results that a synergistic effect is present with these two types of stabilisers.

EXPERIMENT J

Doubled cards were used as in Experiment B but of weight 905 g/m². These double cards were divided into eight series numbered J-0 to J-7. Cards J-0 were each impregnated with 12.5g of DDVP, the other doubled cards were each impregnated with 12.5 g of a solution in DDVP as follows:
J-1: 0.2% of elemental sulphur
J-2: 1.7% of 5-allyl benzodioxole
J-3: 1.5% of 5-allyl benzodioxole + 0.2% of elemental sulphur
J-4: 1.7% of 5-(3-oxo butene-1 yl) benzodioxole
J-5 : 1.5% of 5-(3-oxo butene-1 yl) benzodioxole + 0.2% of elemental sulphur.
J-6: 1.7% of 5-(propene-1 yl) benzodioxole
J-7: 1.5% of 5-(propene-1 yl) benzodioxole + 0.2% of elemental sulphur.

The thus impregnated cards were suspended in a room the temperature of which was kept at 22°±2°C and the relative humidity of which was about 77.

At the end of 21 days the percentage quantities of DDVP destroyed were measured as given in Experiment A and tabulated as follows:

| J-0 | J-1 | J-2 | J-3 | J-4 | J-5 | J-6 | J-7 |
|---|---|---|---|---|---|---|---|
| 45.1 | 9.1 | 1.2 | 0.5 | 7.1 | 1.3 | 0.5 | 0.02 |
| ±0.7 | ±1.8 | ±0.3 | ±0.02 | ±1.3 | ±0.2 | ±0.05 | ±0.00 |

The results of this experiment shown the value of mixtures of stabilisers according to the present invention with a complementary stabiliser such as sulphur. There can, in effect be seen from the results above, a synergistic effect with these two types of stabiliser.

EXPERIMENT K

Double cards were used as in Experiment B but of size 7 × 10 cm. These cards were divided into two series K-0 and K-1. The doubled cards K-0 were each impregnated with 16.6 g of a composition containing 50% by weight DDVP and 50% by weight of a mixture of 3 parts by weight vaseline oil and 1 part by weight stearone.

The double cards K-1 were each impregnated with 16.6 g of the same composition but in which 2.1% of the vaseline oil/stearone mixture, based on the weight of the composition, had been replaced by 2% 5-allyl benzodioxole and 0.1% of 1(4-methyl-2-nitro phenylazo)-3-ethoxycarbonyl-4,4-dimethyl-2,6-dioxo cylohexane.

The so impregnated double cards were each placed in a sachet made from a polyethylene/aluminum complex, the polyethylene face inwards, and the sachets were hermetically sealed by welding. After 8 months storage at 40°C the sachets were opened and their contents submitted to analysis as set out in Experiment A. The percentage quantities of DDVP decomposed were tabulated as follows:

| K-0 | K-1 |
|---|---|
| 16.7 | 4.9 |

EXPERIMENT L

Four series of compositions were prepared containing 50% by weight DDVP; these series were called L-0 to L-3. The composition L-0 contained 50% by weight xylene. The compositions L-1 to L-3 contained the following compounds, the balance to 100% being xylene:

L-1: 2% of 5-allyl benzodioxole
L-2: 1% of elemental sulphur
L-3: 2% of 5-allyl benzodioxole and 1% of elemental sulphur.

These compositions were each enclosed in a sealed flask and placed at a temperature of 60°C; after 36 days, the flasks were opened and their contents analysed in the fashion described in Experiment A. The percentage quantities of DDVP destroyed are tabulated as follows:

| L-0 | L-1 | L-2 | L-3 |
|-----|-----|-----|-----|
| 14.7 | 3.9 | 2.6 | 1.2 |

The results of experiments K and L show the value of the stabilisers of the present invention for preserving phosphoric esters and compositions containing them during storage. It also confirms the value of associating stabilisers according to the invention with other stabilisers.

EXPERIMENT M

Cards of size 5 × 10 cm were used as in Experiment B, but left as a single thickness. These cards were divided into four series M-0 to M-3. The cards M-0 were each impregnated with 6g of 0(2,2-dibromovinyl)-0,0-dimethyl phosphate. The other cards were each impregnated with 6 g of a 2% solution of one of the following compounds in 0-(2,2-dibromovinyl)-0,0-dimethyl phosphate:

M-1 5-(3-oxo-buten-1-yl) benzodioxole
M-2 5-(2-aminopropyl) benzodioxole
M-3 5-(3,6,9-trioxa-undecyl-2-oxy) benzodioxole The thus impregnated cards were suspended in a room the temperature of which was kept at 22° ± 2°C, the relative humidity of which was about 60.

At the end of 16 days the percentage quantities of ester destroyed were measured potentiometrically. Account was taken of the initial acidity present in the phosphoric ester (equivalent to 7.4% of ester) and this was deducted from the results obtained.

| M-0 | M-1 | M-2 | M-3 |
|-----|-----|-----|-----|
| 14.8 | 6.0 | 3.4 | 2.6 |

EXPERIMENT N

Cards of size 5 × 10 cm were used as described in Experiment B, but left at a single thickness. These cards were divided into five series N-0 to N-4. The cards N-0 were each impregnated with 6g of 0(2,2-dichlorovinyl)-0,0-diethvl phosphate. The other cards were each impregnated with 6g of a 2% solution of one of the following compounds in 0(2,2-dichlorovinyl)0,0-diethyl phosphate.

N-1 5(3-oxo-buten-1-yl) benzodioxole
N-2 5(2-aminopropyl) benzodioxole
N-3 5(3,6,9-trioxaundecyl-2-oxy) benzodioxole
N-4 5-allyl benzodioxole.

The thus impregnated cards were suspended in a room the temperture of which was kept at 22° ± 2°C and the relative humidity of which was about 60.

After 48 days, the percentage quantities of ester destroyed were measured as noted in Experiment A and tabulated as follows (initial acidity corresponding to 2.5% of the ester has been deducted):

| N-0 | N-1 | N-2 | N-3 | N-4 |
|-----|-----|-----|-----|-----|
| 7.1 | 2.9 | 1.4 | 4.3 | 2.5 |

Several formulations will now be described in order to illustrate, though not to limit, the scope of the invention. For simplicity of expression, the benzodioxoles used are denoted as follows:

benzodioxole A: 5-allyl benzodioxole (safrole)
benzodioxole B: 5-(propene-1 yl) benzodioxole
benzodioxole C: 5-hydroxy benzodioxole
benzodioxole D: 5-(3,6,9-trioxa undecyl-2 oxy) benzodioxole
benzodioxole E: 5-(3-oxo butene-1 yl) benzodioxole The sulphur compounds used as complementary stabilisers are denoted as follows:

sulphur compound A: 2-mercapto benzothiazole
sulphur compound B: zinc salt of 2-mercapto benzothiazole
sulphur compound C: bis(N,N-dimethylthiocarbamoyl)sulphide
sulphur compound D: bis(N,N-dimethylthiocarbamoyl)disulphide
sulphur compound E: thioacetamide
sulphur compound F: zinc N,N-dimethyldithio carbamate
sulphur compound G: 2-benzothiazolyl disulphide The azoic compounds used as complementary stabilisers are denoted as follows, with the exception of azobenzene which is referred to as such:

diazene A: 1-4(phenylazo phenylazo)2-ethylamino naphthalene
diazene B: 1-(4-methyl-2-nitro phenylazo)-3-ethoxycarbonyl-4,4-dimethyl-2,6-dioxo cyclohexane
diazene C: 1-phenylazo-2-naphthol
diazene D: 1-phenylazo N,N-diethylaniline
diazene E: chromium complex (1 : 2), in admixture of the following azoic compounds:
 1-(2-hydroxy-5-nitro phenylazo)-2-naphthol, sodium salt (0.4 mole)
 1-(2-hydroxy-4-nitro phenylazo)-2-naphthol, sodium salt (0.3 mole)
 1-(2-hydroxy-3-nitro-5-ter, amyl-phenylazo)-2-naphthol sodium salt (0.3 mole)

In the tables in the following examples, values are expressed in weight percent throughout.

EXAMPLES 1 to 10

Insecticidal compositions comprising DDVP as phosphoric ester, and at least one benzodioxole as principal stabiliser therefor, the compositions sometimes also containing a solvent for the ester and/or a complementary stabiliser chosen from sulphur, sulphur compounds, oxiranes, and azoic compounds.

TABLE I

| DDVP | 1<br>99.6 | 2<br>99.5 | 3<br>98 | 4<br>75 | 5<br>79 | 6<br>78 | 7<br>90 | 8<br>67 | 9<br>85 | 10<br>50 |
|---|---|---|---|---|---|---|---|---|---|---|
| dioctylphthalate | — | — | — | 20 | 20 | — | — | — | — | — |
| dibutylsebacate | — | — | — | — | — | 20 | — | — | — | — |
| diisoctyladipate | — | — | — | — | — | — | 9 | 32 | 12 | 47 |
| octyl epoxystearate | — | — | — | 4 | 0.1 | — | — | — | — | — |
| azobenzene | — | — | — | — | 0.1 | — | — | — | — | — |
| diazene E | — | — | — | — | — | 0.5 | — | — | — | — |
| sulphur | 0.2 | — | — | — | — | — | 0.5 | — | — | — |
| sulphur compound A | — | — | — | 0.5 | — | — | — | — | — | — |
| sulphur compound D | — | — | — | — | — | 0.5 | — | — | — | — |
| sulphur compound G | — | — | — | — | — | — | — | — | 2 | — |
| benzodioxole A | — | — | — | — | 0.8 | — | 0.5 | — | — | — |
| benzodioxole B | 0.2 | — | — | 0.5 | — | — | — | 1 | — | — |
| benzodioxole D | — | — | 2 | — | — | — | — | — | 1 | — |
| benzodioxole E | — | 0.5 | — | — | — | 1 | — | — | — | 3 |

EXAMPLES 11 to 20

Insecticidal compositions comprising DDVP as phosphoric ester at least one benzodioxole as principal stabiliser therefor, a vaseline or paraffin oil as solvent, a heavy alkanone as co-solvent, and in some cases a complementary stabiliser chosen from sulphur, sulphur compounds, oxiranes and azoic compounds.

TABLE II

| DDVP | 11<br>50 | 12<br>50 | 13<br>50 | 14<br>60 | 15<br>75 | 16<br>75 | 17<br>40 | 18<br>25 | 19<br>50 | 20<br>50 |
|---|---|---|---|---|---|---|---|---|---|---|
| vaseline oil (a) | — | — | 35 | — | — | — | 43 | — | — | — |
| paraffin oil (a') | 35 | 35 | — | 29 | 17 | 17 | — | 60 | 35 | 35 |
| laurone | — | — | 13 | — | 6 | 6 | — | 12 | — | — |
| palmitone | — | — | — | 10 | — | — | — | — | — | — |
| stearone | 11.9 | 11.9 | — | — | — | — | 14 | — | 12 | 12 |
| epoxidised soya oil | — | — | 1 | — | — | — | — | — | — | 2 |
| diazene B | 0.1 | 0.1 | — | — | — | — | — | 0.5 | — | — |
| diazene C | — | — | — | — | 0.5 | 0.2 | — | — | — | — |
| sulphur | 1 | 1 | — | — | — | — | — | — | — | 0.1 |
| sulphur compound D | — | — | — | — | 0.5 | — | — | — | — | — |
| sulphur compound E | — | — | — | — | — | 0.8 | — | — | — | — |
| sulphur compound F | — | — | 0.05 | — | — | — | — | — | — | — |
| benzodioxole A | 2 | — | — | — | — | 1 | — | — | 3 | — |
| benzodioxole B | — | 2 | 0.95 | — | — | — | — | 1 | — | 0.9 |
| benzodioxole C | — | — | — | 1 | — | — | 0.3 | 0.5 | — | — |
| benzodioxole E | — | — | — | — | 1 | — | 2.7 | 1 | — | — |

(a) semi-refined oil having a density of 0.867 at 15°C and a freezing point of about −42°C.
(a') semi-refined product having a density of 0.870 at 15°C and a viscosity of 1.7° Engler at 50°C.

EXAMPLES 21 to 30

Insecticidal compositions comprising DDVP a phosphoric ester, at least one benzodioxole as principal stabiliser for this ester, a solid or semi-solid adjuvant chosen from paraffin, vaseline and petrolatum, a solvent chosen from heavy alkanones and in some cases a complementary stabiliser chosen from sulphur, sulphur compounds, oxiranes and azoic compounds.

EXAMPLES 31 to 40

Insecticidal compositions usable to wick evaporators formed by a reservoir and a wick dipping into the composition and having a part open to the atmosphere.

These compositions comprise DDVP as phosphoric ester, a solvent for the ester chosen from alkanes, a co-solvent chosen from 1-chlorodecane, 3,6,9-trioxaundecane and 5,8,11-trioxapentadecane, at least one benzodioxole as principal stabiliser for the phosphoric ester and in some cases a complementary stabiliser chosen from sulphur, sulphur compounds, oxiranes and azoic compounds.

TABLE III

| DDVP | 21<br>15 | 22<br>15 | 23<br>20 | 24<br>20 | 25<br>20 | 26<br>20 | 27<br>28 | 28<br>28 | 29<br>32 | 30<br>33 |
|---|---|---|---|---|---|---|---|---|---|---|
| ordinary paraffin 60/62° | — | — | 53 | 53 | 54 | 54 | — | — | — | — |
| ordinary paraffin 52/54° | 64.5 | 63 | — | — | — | — | — | — | — | — |
| vaseline (b) | — | — | — | — | — | — | — | — | 30 | 32 |
| petrolatum (b') | — | — | — | — | — | — | 35 | 35 | — | — |
| laurone | 19 | 18.5 | 24.5 | 24.8 | 24.5 | 24 | — | — | — | — |
| stearone | — | — | — | — | — | — | 36 | 36 | 37 | 34 |
| epichlorhydrin | — | 3 | — | — | — | — | — | — | 0.6 | — |
| diazene D | — | — | — | — | — | — | — | 0.2 | — | — |
| azobenzene | — | — | — | 2 | — | — | — | — | 0.2 | — |
| sulphur | — | — | — | — | 1.2 | — | — | — | — | — |
| sulphur compound B | — | — | — | — | — | — | 0.3 | — | — | — |
| sulphur compound C | — | — | — | — | — | — | — | 0.2 | — | — |
| sulphur compound G | — | — | 2 | — | — | — | — | — | 0.2 | — |
| benzodioxole A | — | 0.5 | — | — | — | 2 | — | — | — | — |
| benzodioxole B | — | — | 0.5 | — | 0.3 | — | — | — | — | 1 |
| benzodioxole C | — | — | — | 0.2 | — | — | — | — | 0.6 | — |
| benzodioxole E | 1.5 | — | — | — | — | — | — | 0.7 | — | — |

(b) yellow-colored technical product having a dropping point above 47°C.
(b') maroon-colored technical product having a dropping point of about 72°C.

TABLE IV

| DDVP | 31<br>9.2 | 32<br>10.6 | 33<br>9.2 | 34<br>8.5 | 35<br>9.7 | 36<br>10.6 | 37<br>7.8 | 38<br>9.2 | 39<br>7.8 | 40<br>10.6 |
|---|---|---|---|---|---|---|---|---|---|---|
| n-dodecane | — | — | — | 86 | 85 | — | 86 | — | 86 | — |
| "Isopar L" (C″) | 85.3 | 84 | 86 | — | — | 84 | — | 86.4 | — | 84 |
| 1-chloro decane | — | — | 4 | — | — | — | 6 | — | 6 | — |
| 3,6,9-trioxa undecane (c) | 5 | 5 | — | — | — | 5 | — | — | — | 5 |
| 5,8,11-trioxa pentadecane (c′) | — | — | — | 5 | 5 | — | — | 4 | — | — |
| epoxidised soya oil | — | — | — | 0.4 | — | — | — | — | — | 0.25 |
| diazene A | 0.04 | 0.05 | — | — | — | — | — | — | 0.04 | — |
| azobenzene | — | 0.1 | — | — | — | — | 0.1 | — | — | 0.05 |
| sulphur | — | — | — | — | 0.03 | — | — | — | — | — |
| sulphur compound A | — | — | — | — | — | 0.1 | — | — | 0.06 | — |
| benzodioxole B | 0.46 | — | 0.8 | — | — | — | 0.1 | — | — | 0.1 |
| benzodioxole C | — | 0.25 | — | — | 0.27 | — | — | — | 0.1 | — |
| benzodioxole E | — | — | — | 0.1 | — | 0.3 | — | 0.4 | — | — | c) reinforcing solvent known as diglycoldiethyl ether, and sold under the Trade Mark "Diethylcarbitol" by the U.S. Company Union Carbide Chemicals Co. of New York.
c′) reinforcing solvent known as diglycol dibutyl ether, sold under the Trade Mark "Dibutylcarbitol" by the Union Carbide Chemicals Co. aforementioned.
c″) distillation cut between 189° and 205°C of branched aliphatic hydrocarbons obtained by synthesis, containing a mixture of decane, undecane and dodecane, sold by the company Esso Standard.

EXAMPLES 41 to 50

Insecticidal compositions comprising DDVP as phosphoric ester, at least one benzodioxole as principal stabiliser therefor, an odorant material from linaol, ionone, menthone, linalyl acetate, orange terpenes and citron terpenes and in some cases a complementary stabiliser chosen from sulphur, suplhur compounds, oxiranes and azoic compounds.

EXAMPLES 51 to 60

Insecticidal compositions comprising DDVP as phosphoric ester, at least one benzodioxole as principal stabiliser, a synthetic thermoplastic resin as solid solvent, a heavy ester used as complementary solvent acting at the same time, in some cases as a plasticiser for the resin, and in several cases as complementary stabiliser chosen from sulphur, sulphur compounds, oxiranes and azoic compounds.

TABLE V

| DDVP | 41<br>79 | 42<br>77 | 43<br>86 | 44<br>72 | 45<br>83 | 46<br>85 | 47<br>68 | 48<br>77 | 49<br>72 | 50<br>87 |
|---|---|---|---|---|---|---|---|---|---|---|
| linalol | 7.5 | — | — | — | — | — | — | — | — | — |
| α-ionone | — | 20 | 10 | 5 | — | — | — | — | — | — |
| menthone | — | — | — | — | 15 | — | — | — | — | — |
| linalyl acetate | 7.5 | — | — | — | — | 12 | — | — | — | — |
| orange terpenes | — | — | — | 20 | — | — | 30 | 20 | — | — |
| citron terpenes | — | — | — | — | — | — | — | — | 25 | 12 |
| epoxidised soya oil | 5 | — | — | 2 | — | — | — | — | — | — |
| diazene A | — | 0.5 | — | — | — | — | — | — | — | — |
| diazene B | — | — | — | 0.5 | — | — | — | — | — | — |
| sulphur | — | — | — | — | — | — | 0.1 | — | — | — |
| sulphur compound D | — | — | — | — | — | — | — | — | 1 | — |
| benzodioxole A | 1 | — | — | — | — | 1.5 | — | — | — | — |
| benzodioxole B | — | — | — | 0.5 | — | — | — | 3 | — | — |
| benzodioxole C | — | — | — | — | 2 | 1.5 | — | — | — | 1 |
| benzodioxole D | — | — | — | — | — | — | 1.9 | — | 2 | — |
| benzodioxole E | — | 2.5 | 4 | — | — | — | — | — | — | — |

TABLE VI

| DDVP | 51<br>20 | 52<br>25 | 53<br>30 | 54<br>20 | 55<br>20 | 56<br>25 | 57<br>20 | 58<br>25 | 59<br>30 | 60<br>30 |
|---|---|---|---|---|---|---|---|---|---|---|
| polyvinyl chloride | 56 | 62 | 40 | 62 | 60 | 50 | 60 | — | — | — |
| ethylene/vinyl acetate copolymer (d) | — | — | — | — | — | — | — | 54 | — | — |
| vinyl acetate/vinyl chloride copolymer (10:90) | — | — | — | — | — | — | — | — | 50 | 54 |
| diisooctyl adiphate | 23 | — | — | — | — | — | 9 | — | — | — |
| tricresyl phosphate | — | 10 | 29 | 12 | — | — | — | — | 19 | 5 |
| methyl laurate | — | — | — | 5 | 9 | — | — | — | — | — |
| dioctyl phthalate | — | — | — | — | 9 | 8 | — | 10 | — | — |
| dimethyl succinate | — | — | — | — | — | 15 | 9 | — | — | — |
| dimethyl maleate | — | — | — | — | — | — | — | 10 | — | 10 |
| octyl epoxystearate | — | — | — | — | 1.5 | — | — | — | — | — |
| diazene C | — | 0.2 | — | — | — | — | — | — | 0.1 | — |
| sulphur | — | — | 0.2 | — | — | — | — | — | — | — |
| sulphur compound B | — | 0.3 | — | — | — | — | 0.4 | — | — | — |
| sulphur compound D | — | — | — | — | 0.3 | — | — | — | — | — |
| benzodioxole B | 1 | — | — | — | — | 0.2 | — | 1.6 | 0.4 | 0.9 | 0.5 |
| benzodioxole C | — | — | 0.8 | 1 | — | 2 | — | — | — | 0.5 |
| benzodioxole E | — | 2.5 | — | — | — | — | — | — | 0.6 | — |

(d) copolymer of 67% ethylene and 33% vinyl acetate having an intrinsic viscosity of 0.78 for 0.25 g in 100 ml toluene at 30°C.

EXAMPLES 61 to 70

Insecticidal compositions comprising DDVP as phosphoric ester, at least one benzodioxole as principal stabiliser therefor, a paraffin as solid adjuvant, a fossil silica as mineral adjuvant, and, in some cases, a complementary stabiliser chosen from sulphur, suplhur compounds, oxiranes and azoic compounds, an ethylene/vinyl acetate copolymer as an agent improving the mechanical properties of the paraffin, a pigment and/or a modified montmorillonite as dispersant allowing the composition to remain homogeneous before cooling.

TABLE VII

| DDVP | 61<br>24.25 | 62<br>24 | 63<br>24 | 64<br>25 | 65<br>25 | 66<br>24 | 67<br>24 | 68<br>25 | 69<br>25 | 70<br>20 |
|---|---|---|---|---|---|---|---|---|---|---|
| paraffin 60/62° | 64 | 65 | 65 | 57 | 57 | 57 | 56 | 52 | 51 | 68 |
| ethylene/vinyl acetate copolymer (71:29) | — | — | — | — | — | — | — | 12 | 12 | — |
| diatomaceous earth | — | — | — | 15 | 15 | 12 | 12 | 10 | 10 | 10 |
| amine oleate (e') | — | — | — | — | — | 5 | 5 | — | — | — |
| modified montmorillonite (e'') | 9 | 9 | 9 | 1 | 1 | — | — | — | — | — |
| pigment (e) | 0.5 | 0.5 | 0.5 | — | 0.8 | — | 1 | — | 0.6 | 0.8 |
| cyclohexyl epoxystearte | — | — | — | — | 0.7 | — | — | — | — | — |
| azobenzene | — | — | — | — | — | 1 | — | — | — | — |
| diazene B | — | — | 0.4 | — | — | — | — | 0.5 | — | — |
| sulphur | — | — | — | 1 | — | — | — | — | — | — |
| sulphur compound B | — | 0.2 | — | — | — | — | — | — | 0.4 | — |
| sulphur compound F | — | — | 0.3 | — | — | — | — | — | — | — |
| benzodioxole A | 2.25 | — | — | 1 | — | — | — | 0.5 | — | 1.2 |
| benzodioxole B | — | 1.3 | — | — | — | 1 | — | — | — | — |
| benzodioxole E | — | — | 0.8 | — | 0.5 | — | 2 | — | 1 | — | e) yellow Irgalith BAW
e') product formed by reaction, in a molecular ratio of 2:1 between oleic acid and a mixture of the following diamines:
hexadecylaminopropylene amine (10%)
octadecylamino propylene amine (50%)
octadecylamine propylene amine (85%)
e'') mixture of dimethyl dihexadecylammonium montmorillonite (70%) and dimethyl dioctadecylammonium montmorillonite.

It is clear that the invention is not limited to the formulations just set forth, which are merely given as examples of the manifold possibilities of use of the invention. In particular, the DDVP of these formulations can be replaced by a phosphoric ester chosen from:

1. 2,2-dichloro vinyl dimethyl phosphate
2. 2,2-dichloro vinyl diethyl phosphate
3. 2,2-dichloro vinyl dipropyl phosphate
4. 2,2-dibromo vinyl dimethyl phosphate
5. 2,2-dibromo vinyl diethyl phosphate
6. 2,2-dibromo vinyl dipropyl phosphate
7. 2-bromo-2-chloro vinyl dimethyl phosphate
8. 2-bromo-2-chloro vinyl diethyl phosphate
9. 2,2-dichloro vinyl, ethyl methyl phosphate
10. 1,2-dibromo-2,2-dichloro ethyl dimethyl phosphate
11. 1,2-dibromo-2,2-dichloro ethyl diethyl phosphate
12. 1-bromo-2,2,2-trichloro ethyl dimethyl phosphate
13. 1-bromo-2,2,2-trichloro ethyl diethyl phosphate
14. 1,2,2,2-tetrabromo ethyl dimethyl phosphate
15. 1,2,2,2-tetrabromo ethyl diethyl phosphate
16. 1,2-dibromo-2,2-dichloro propyl dimethyl phosphate
17. 1,2-dibromo-2,2-dichloro propyl diethyl phosphate
18. 2,2-dichloro 1-methyl vinyl dimethyl phosphate
19. 2,2-dichloro 1-methyl vinyl diethyl phosphate and the corresponding thiophosphates, for example
20. 2,2-dichloro vinyl dimethyl thiophosphate.

We claim:

1. An insecticide evaporator comprising:
I. a solid or liquid insecticidal composition containing
A. an insecticidally effective amount of an insecticidal phosphate selected from the group consisting of
   2,2-dichloro vinyl dimethyl phosphate
   2,2-dichloro vinyl diethyl phosphate
   2,2-dichloro vinyl dipropyl phosphate
   2,2-dibromo vinyl dimethyl phosphate
   2,2-dibromo vinyl diethyl phosphate
   2,2-dibromo vinyl dipropyl phosphate
   2-bromo-2-chloro vinyl dimethyl phosphate
   2-bromo-2-chloro vinyl diethyl phosphate
   2,2-dichloro vinyl, ethyl methyl phosphate
   2,2-dichloro 1-methyl vinyl dimethyl phosphate
   and
   2,2-dichloro 1-methyl vinyl diethyl phosphate,
wherein on contact with molecules of water at least partial decomposition of the ester takes place by protonization, said vinyl phosphate optionally being admixed with a solid or liquid solvent, B. about 0.1 to 10%, based on the weight of said volatile phosphate, of a 1,3-benzodioxole capable of stabilizing said phosphate against decomposition by protonization, said benzodioxole having no action as a toxicity synergist for the insecticidal phosphate in said proportions, and selected from the group consisting of at least one compound of the formula

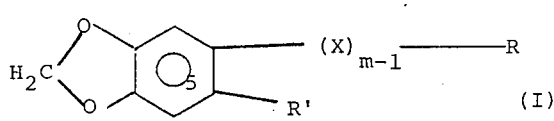

wherein $m$ is 1 or 2, and X is an alkylene bridge of 1 or 2 or an alkenylene bridge of 2 carbon atoms, and R' is
a. hydrogen or
b. lower alkyl and
A. When $m$ represents 1 in formula (I) R represents
a. hydrogen
b. lower alkyl
c. lower alkenyl d. halogen of atomic number not exceeding 17
e. nitro
f. the group

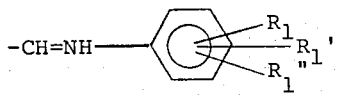

in which each of $R_1$, $R_1'$ and $R_1''$, independently of the others, is the same or a different group selected from the group consisting of hydrogen, lower alkyl, lower alkoxy, chloro and bromo;

g. the group

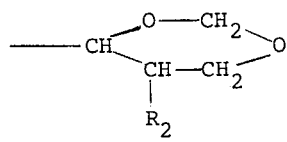

in which $R_2$ is hydrogen or lower alkyl, or h. the group

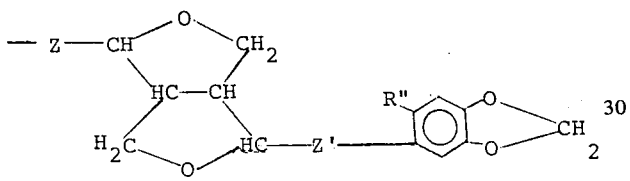

in which Z and Z' are each independently a C—C bond or an oxygen atom (—O—) and R'' is hydrogen, lower alkyl or lower alkoxy, and B. when $m$ represents 1 or 2 in formula (I) R represents
i. cyano
ii. the group

wherein $R_4$ is hydrogen, or lower alkyl and $R_5$ is hydrogen or lower alkyl, iii. the group —CO—$R_6$ in which $R_6$ is
a. hydrogen
b. —OM in which M is hydrogen or an equivalent metal cation or a quaternary ammonium cation
c. lower alkyl
d. lower alkoxy
e. phenyl, unsubstituted or substituted by one or more of the following substituents: lower alkyl, lower alkoxy, chloro, or bromo; or
f. the group

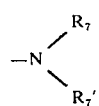

wherein each of $R_7$ and $R_7'$ is independently selected from hydrogen or lower alkoxy iv. the group

v. alkyl
in which the alkyl group has 1 to 8 carbon atoms
v. the group —O—$R_8$
in which $R_8$ is lower alkyl or oxa alkyl of at most 15 carbon atoms and 3 oxygen atoms in the chain,
vi. the group

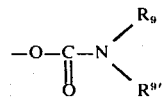

in which each of $R_9$ and $R_9'$ independently is hydrogen, lower alkyl or phenyl or
vii. nitro C. when $m$ represents 1 in formula (I):
R and R' taken together represent one of the following divalent groups:
a. the group

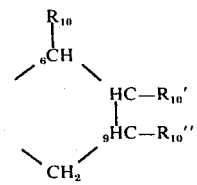

in which each of $R_{10}$, $R_{10}'$ and $R_{10}''$ independently is hydrogen, lower alkyl, alkoxycarbonyl of 2 to 5 carbon atoms, or the group —COOM, M having the meaning given above, or
b. the group

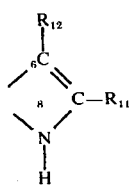

in which $R_{11}$ is
hydrogen, lower alkyl, lower alkoxy or pyrrolidino, and $R_{12}$ represents
hydrogen or lower alkyl, c. at least one secondary agent for stabilizing said phosphate against decomposition by protonization selected from:
$C_1$ about 0.05 to 6%, based on the weight of said vinyl phosphate, of elemental sulphur or
$C_2$ about 0.05 to 10% by weight based on the weight of said vinyl phosphate of a divalent sulfur compound,
II. a solid fibrous support absorbent for the composition (I) formed of a felt of wool, a cellulosic fiber material or a cardboard of glass fibers.

2. An insecticide evaporator as described in claim 1, wherein the proportion of the stabilizing agent defined under (B) is 0.5 to 6% of the weight of the phosphoric ester.

3. An insecticide evaporator as described in claim 1, further comprising an epoxidized compound which is selected from the group consisting of octylepoxystearate, cyclohexylepoxystearate, epoxidized soya bean oil and epichlorhydrin and said epoxidized compound is present in a proportion of 0.1 to 20% based on the weight of said volatile phosphoric ester.

4. An insecticide evaporator as described in claim 1, wherein said fibrous material is cardboard.

5. An insecticide evaporator as described in claim 4, further comprising a membrane permeable to said insecticidal phosphate coating said support.

6. An insecticide evaporator as described in claim 5, wherein said permeable membrane is constituted by a layer of polyethylene, polypropylene or a mixture thereof, a copolymer of ethylene and propylene or a copolymer comprising vinylidene chloride.

7. An insecticide evaporator as described in claim 5, wherein said permeable membrane is constituted by a layer of polyethylene of a thickness of from 10 to 80 microns.

8. An insecticide evaporator as described in claim 1, wherein said stabilizing agent consists essentially of
   i. the 1,3-benzodioxole and
   ii. elemental sulphur.

9. An insecticide evaporator as decribed in claim 1, wherein said stabilizing agent is a composite agent comprising
   i. the 1,3-benzodioxole and
   ii. a compound of divalent sulphur.

* * * * *